United States Patent
Pillarisetti et al.

(10) Patent No.: US 6,610,726 B2
(45) Date of Patent: Aug. 26, 2003

(54) COMPOSITIONS AND AGENTS FOR MODULATING CELLULAR PROLIFERATION AND ANGIOGENESIS

(75) Inventors: Sivaram Pillarisetti, Norcross, GA (US); Itzhak D. Goldberg, Englewood, NJ (US)

(73) Assignee: North Shore-Long Island Jewish Research Institute, Manhasset, NY (US)

( * ) Notice: Subject to any disclaimer, the term of this patent is extended or adjusted under 35 U.S.C. 154(b) by 0 days.

(21) Appl. No.: 10/026,672

(22) Filed: Dec. 19, 2001

(65) Prior Publication Data

US 2003/0022924 A1 Jan. 30, 2003

Related U.S. Application Data

(63) Continuation-in-part of application No. 09/896,832, filed on Jun. 29, 2001.

(51) Int. Cl.$^7$ .............................................. A61K 31/415

(52) U.S. Cl. ................... 514/406; 514/407; 548/365.7; 548/364.1; 548/374.1; 548/373.1; 548/376.1

(58) Field of Search ................................ 514/406, 407; 548/365.7, 374.1, 373.1, 370.1

(56) References Cited

U.S. PATENT DOCUMENTS

| | | | | | |
|---|---|---|---|---|---|
| 6,162,819 | A | * | 12/2000 | Schindler et al. | ........... 514/405 |
| 6,403,630 | B1 | * | 6/2002 | Dannenberg et al. | .... 424/138.1 |
| 2002/0077344 | A1 | * | 6/2002 | Heitsch et al. | ............. 514/406 |

* cited by examiner

*Primary Examiner*—James H Reamer
(74) *Attorney, Agent, or Firm*—Klauber & Jackson

(57) ABSTRACT

The invention is directed to pharmaceutical compositions containing small organic molecules having the ability to mimic or agonize hepatocyte growth factor/scatter factor (HGF/SF) activity, useful for promoting, for example, vascularization of tissues or organs for promoting wound or tissue healing, or augmenting or restoring blood flow to ischemic tissues such as the heart following myocardial infarction.

12 Claims, 8 Drawing Sheets

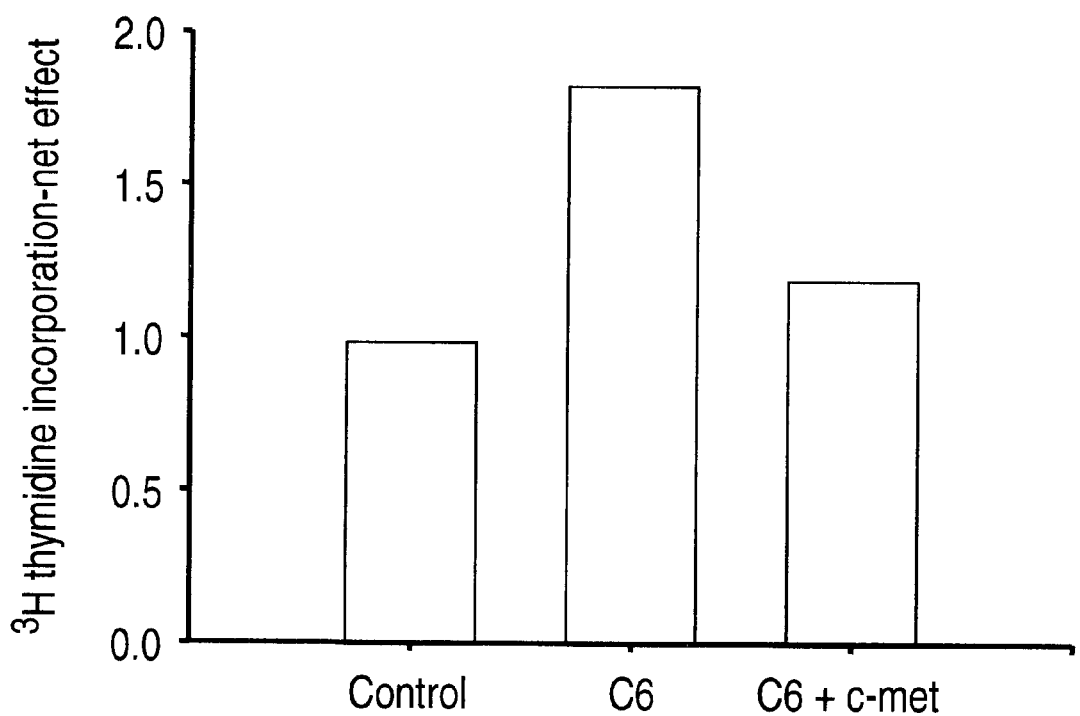

Effect of
(4-chlorophenyl)[3-(2-(2-thienyl)vinyl)-1H-pyrazol-1-yl]
methone on HUVEC proliferation Creatinine changes Mouse serum creatinine assay

COMPOSITIONS AND AGENTS FOR MODULATING CELLULAR PROLIFERATION AND ANGIOGENESIS

CROSS-REFERENCE TO RELATED APPLICATION

This application is a continuation-in-part of Ser. No. 09/896,832, filed Jun. 29, 2001, which is incorporated herein by reference in its entirety.

BACKGROUND OF THE INVENTION

Scatter factor (SF; also known as hepatocyte growth factor [HGF], and hereinafter referred to and abbreviated as HGF/SF) is a pleiotropic growth factor that stimulates cell growth, cell motility, morphogenesis and angiogenesis. HGF/SF is produced as an inactive monomer (~100 kDa) which is proteolytically converted to its active form. Active HGF/SF is a heparin-binding heterodimeric protein composed of a 62 kDa α chain and a 34 kDa β chain. HGF/SF is a potent mitogen for parenchymal liver, epithelial and endothelial cells (Matsumoto, K, and Nakamura, T., 1997, Hepatocyte growth factor (HGF) as a tissue organizer for organogenesis and regeneration. Biochem. Biophys. Res. Commun. 239, 639–44; Boros, P. and Miller, C. M., 1995, Hepatocyte growth factor: a multifunctional cytokine. Lancet 345, 293–5). It stimulates the growth of endothelial cells and also acts as a survival factor against endothelial cell death (Morishita, R, Nakamura, S, Nakamura, Y, Aoki, M, Moriguchi, A, Kida, I, Yo, Y, Matsumoto, K, Nakamura, T, Higaki, J, Ogihara, T, 1997, Potential role of an endothelium-specific growth factor, hepatocyte growth factor, on endothelial damage in diabetes. Diabetes 46:138–42). HGF/SF synthesized and secreted by vascular smooth muscle cells stimulate endothelial cells to proliferate, migrate and differentiate into capillary-like tubes in vitro (Grant, D. S, Kleinman, H. K., Goldberg, I. D., Bhargava, M. M., Nickoloff, B. J., Kinsella, J. L., Polverini, P., Rosen, E. M., 1993, Scatter factor induces blood vessel formation in vivo. Proc. Natl. Acad. Sci. U S A 90:1937–41; Morishita, R., Nakamura, S., Hayashi, S., Taniyama, Y., Moriguchi, A., Nagano, T., Taiji, M., Noguchi, H., Takeshita, S., Matsumoto, K., Nakamura, T., Higaki, J., Ogihara, T., 1999, Therapeutic angiogenesis induced by human recombinant hepatocyte growth factor in rabbit hind limb ischemia model as cytokine supplement therapy. Hypertension 33:1379–84). HGF/SF-containing implants in mouse subcutaneous tissue and rat cornea induce growth of new blood vessels from surrounding tissue. HGF/SF protein is expressed at sites of neovascularization including in tumors (Jeffers, M., Rong, S., Woude, G. F., 1996, Hepatocyte growth factor/scatter factor-Met signaling in tumorigenicity and invasion/metastasis. J. Mol. Med. 74:505–13; Moriyama, T., Kataoka, H., Koono, M., Wakisaka, S., 1999, Expression of hepatocyte growth factor/scatter factor and its receptor c-met in brain tumors: evidence for a role in progression of astrocytic tumors Int. J. Mol. Med. 3:531–6). These findings suggest that HGF/SF plays a significant role in the formation and repair of blood vessels under physiologic and pathologic conditions. Further discussion of angiogenic proteins may be found in U.S. Pat. Nos. 6,011,009 and 5,997,868, both of which are incorporated herein by reference in their entireties.

Modulation of cellular proliferation by exogenously-supplied therapeutic agents has been offered as a new approach for the prophylaxis and/or treatment of various conditions and diseases in which limited cellular proliferation is responsible for pathology, or at least for the prolongation of rebound from a pathological state to homeostasis. For example, the duration of wound healing, normalization of myocardial perfusion as a consequence of chronic cardiac ischemia or myocardial infarction, development or augmentation of collateral vessel development after vascular occlusion or to ischemic tissues or organs, and vascularization of grafted or transplanted tissues, organs, or wound healing, may be accelerated by promoting cellular proliferation, particularly of vascular cells.

It is toward compounds with HGF/SF-like activity and pharmaceutical compositions comprising them for the prophylaxis and treatment of various conditions and diseases benefiting from HGF/SF activity that the present invention is directed.

The citation of any reference herein should not be construed as an admission that such reference is available as "Prior Art" to the instant application.

SUMMARY OF THE INVENTION

The present invention is directed generally to compositions and pharmaceutical compositions comprising effective amounts of compounds that modulate hepatocyte growth factor/scatter factor (HGF/SF) activities in a mammal, the compounds being useful for the prophylaxis or treatment of any of a number of conditions or diseases in which HGF/SF has a therapeutically useful role. The compounds of the invention generally exhibit HGF/SF stimulatory or agonist activity.

The invention is directed to pharmaceutical compositions comprising a compound that modulates HGF/SF activity with the general formula I:

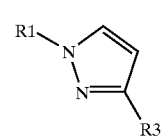

Formula I wherein
R1 is SO$_2$Alkyl, SO$_2$-Aryl, COAlkyl, COAryl, CONHAlkyl; or CONHAryl; and
R3 is CHCH-heteroaryl; phenoxyphenyl; heteroaryl; or Aryl substituted heteroaryl; and a pharmaceutically-acceptable carrier, excipient or diluent.

Non-limiting examples of compounds of Formula I include
(4-chlorophenyl)[3-(2-(2-thienyl)vinyl)-1H-pyrazol-1-yl]methanone;
1-(methylsulfonyl)-3-(2-(2-thienyl)vinyl)-1H-pyrazole;
2,2-dimethyl-1-(3-(2-(2-thienyl)vinyl)-1H-pyrazole-1-yl)propan-1-one;
N-methyl-3-(2-(2-thienyl)vinyl)-1H-pyrazole-1-carboxamide;
(4-chlorophenyl)(3-(3-phenylisoxazol-5-yl)-1H-pyrazol-1-yl)methanone;
(4-chlorophenyl)(3-(3-(4-chlorophenyl)-5-methylisoxazol-4-yl)-1H-pyrazol-1-yl)methanone;
(4-chlorophenyl)(3-(5-(2-thienyl)-2-thienyl)-1H-pyrazol-1-yl)methanone;
(2,4-dichlorophenyl)(3-(5-(2,4-difluorophenyl)-2-furyl)-1H-pyrazol-1-yl)methanone;
N1-phenyl-3-(2-(2-thienyl)vinyl)-1H-pyrazole-1-carboxamide;

(4-chlorophenyl)(3-(2-(5-(2-thienyl)-2-thienyl)-4-methyl-1,3-thiazol-5-yl)-1H-pyrazol-1-yl-methanone;

(3-benzhydryl-1H-pyrazol-1-yl)(4-chlorophenyl)methanone;

N1-(4-chlorophenyl)-3-(2-(2-thienyl)vinyl)-1H-pyrazole-1-carboxamide;

(4-chlorophenyl)(3-(2-methylimidazo(1,2-a)pyridin-3-yl)-1H-pyrazol-1-yl)methanone;

2-chloro-6-(4-(1-(4-chlorobenzyl)-1H-pyrazol-3-yl)phenoxy)benzonitrile; and 1-((4-chlorophenyl)sulfonyl)-3-(2-(2-thienyl)vinyl)-1H-pyrazole.

The compounds comprising the pharmaceutical compositions of the invention have been found to mimic or agonize the biological activities of HGF/SF, and thus are useful in the prophylaxis or treatment, for example, of conditions or diseases in which enhanced cellular or vascular proliferation is desirable, among other desirable activities of HGF/SF. Such conditions or diseases include hepatic disease, renal disease, bone regeneration dysfunction, poor hair growth, wound or tissue healing, treatment of various ischemic diseases, including but not limited to augmenting or restoring blood flow to ischemic tissues such as the heart following myocardial infarction as well as in diabetes-related ischemic conditions. The compounds are also useful in the treatment of atherosclerosis, including reduction of lipid accumulation in the vasculature. Such compounds may be administered in appropriate pharmaceutical compositions either systemically or locally to particular tissues or organs, in order to achieve the desired systemic or local effect. Such desirable activities also include induction of proliferation of endothelial cells, induction of anti-apoptotic activity, induction of scatter activity, or any combination of the foregoing activities. In a preferred embodiment, any one of these activities by a compound of the invention is reduced or inhibited in the presence of exogenous c-met receptor. Compounds of Formula I may be formulated into a suitable pharmaceutical composition for delivery as appropriate, the pharmaceutical composition containing at least one of the compounds of Formula I together with a pharmaceutically-appropriate carrier, excipient or diluent, or combinations of the foregoing. The invention is also directed to pharmaceutical dosage forms comprising an effective amount of a compound of Formula I for administration on a periodic basis, such as four times a day, three times a day, twice a day, and once a day, as well as less frequent dosing, to provide an effective amount of the compound for its intended pharmacological activity. Dosage forms administratable orally, as well as parenteral dosage forms, are embraced herein.

The invention is also directed to compounds of general formula I:

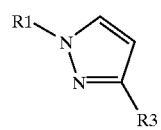

Formula I wherein

R1 is SO$_2$Alkyl, SO$_2$-Aryl, COAlkyl, COAryl, CONHAlkyl; or CONHAryl; and

R3 is CHCH-heteroaryl; phenoxyphenyl; heteroaryl; or Aryl substituted heteroaryl.

Non-limiting examples of compounds of Formula I include (4-chlorophenyl)[3-(2-(2-thienyl)vinyl)-1H-pyrazol-1-yl]methanone;

1-(methylsulfonyl)-3-(2-(2-thienyl)vinyl)-1H-pyrazole;

2,2-dimethyl-1-(3-(2-(2-thienyl)vinyl)-1H-pyrazole-1-yl)propan-1-one;

N-methyl-3-(2-(2-thienyl)vinyl)-1H-pyrazole-1-carboxamide;

(4-chlorophenyl)(3-(3-phenylisoxazol-5-yl)-1H-pyrazol-1-yl)methanone;

(4-chlorophenyl)(3-(3-(4-chlorophenyl)-5-methylisoxazol-4-yl)-1H-pyrazol-1-yl)methanone;

(4-chlorophenyl)(3-(5-(2-thienyl)-2-thienyl)-1H-pyrazol-1-yl)methanone;

(2,4-dichlorophenyl)(3-(5-(2,4-difluorophenyl)-2-furyl)-1H-pyrazol-1-yl)methanone;

N1-phenyl-3-(2-(2-thienyl)vinyl)-1H-pyrazole-1-carboxamide;

(4-chlorophenyl)(3-(2-(5-(2-thienyl)-2-thienyl)-4-methyl-1,3-thiazol-5-yl)-1H-pyrazol-1-yl-methanone;

(3-benzhydryl-1H-pyrazol-1-yl)(4-chlorophenyl)methanone;

N1-(4-chlorophenyl)-3-(2-(2-thienyl)vinyl)-1H-pyrazole-1-carboxamide;

(4-chlorophenyl)(3-(2-methylimidazo(1,2-a)pyridin-3-yl)-1H-pyrazol-1-yl)methanone;

2-chloro-6-(4-(1-(4-chlorobenzyl)-1H-pyrazol-3-yl)phenoxy)benzonitrile; and 1-((4-chlorophenyl)sulfonyl)-3-(2-(2-thienyl)vinyl)-1H-pyrazole.

The invention is also directed to methods for preventing or treating a disease in a mammal in which HGF/SF activity is desirable comprising administering to the mammal an effective amount of a pharmaceutical composition comprising a compound of Formula I as described hereinabove. By way of non-limiting example, conditions and diseases in which HGF/SF activity is desirable include hepatic disease, ischemic and toxin-induced renal disease, dysfunction in bone regeneration, poor hair growth, adverse wound or tissue healing, and ischemic diseases. For example, augmenting or restoring blood flow to ischemic tissues such as the heart following myocardial infarction as well as in diabetes-related ischemic conditions are amenable to treatment using the compounds of the invention. The compounds are also useful in the treatment of atherosclerosis, including reduction of lipid accumulation in the vasculature. Such desirable activities also include induction of proliferation of endothelial cells, induction of anti-apoptotic activity, induction of scatter activity, or any combination of the foregoing activities. In a preferred embodiment, any one of these activities by a compound of the invention is reduced or inhibited in the presence of exogenous c-met receptor.

These and other aspects of the present invention will be better appreciated by reference to the following drawings and Detailed Description.

BRIEF DESCRIPTION OF THE DRAWINGS

FIG. 1 depicts the stimulation of endothelial cell proliferation by (4-chlorophenyl)[3-(2-(2-thienyl)vinyl)-1H-pyrazol-1-yl]methanone, a compound of the invention with HGF/SF-like activity, and the inhibition of the observed stimulation by inclusion of c-met.

DETAILED DESCRIPTION OF THE INVENTION

Figure 2A:
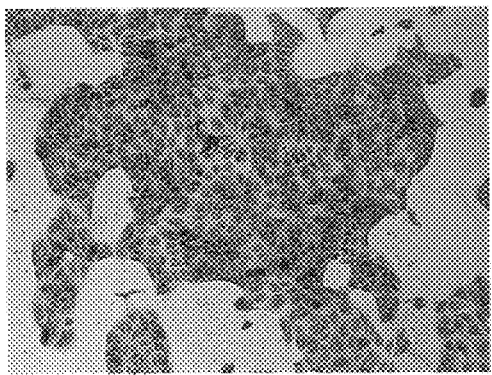
FIGS. 2 A–B show the induction of scatter of MDCK cells by (4-chlorophenyl)[3-(2-(2-thienyl)vinyl)-1H-pyrazol-1-yl]methanone.

The pharmaceutical compositions of the invention comprise agents or compounds which modulate cellular proliferation to provide new and effective agents for the prophylaxis and/or treatment of various conditions and diseases in which limited cellular proliferation is responsible for patholoy, or in which increased cellular proliferation is desirable in the prophylaxis or treatment of the condition or disease. Such compounds may be formulated into pharmaceutical compositions for administration to a mammalian animal, preferably a human, for the treatment of a condition or disease.

For example, the duration of wound healing, vascularization of a damaged and/or ischemic organs, transplants or grafts, normalization of myocardial perfusion as a consequence of chronic cardiac ischemia or myocardial infarction, development or augmentation of collateral vessel development after vascular occlusion or to ischemic tissues or organs, and vascularization of grafted or transplanted tissues, organs, or wound healing, may be accelerated by promoting cellular proliferation, particularly of vascular cells, by administration of a pharmaceutical composition of the invention. Further utility is in the promotion of endothelial growth in vascular grafts and transplants. Treatment of diabetic ischemic disease is a further condition amenable to treatment by the compounds of the invention. Pharmaceutical compositions of the invention possess such activities.

As noted above, modulating cellular proliferation, either by promoting the growth or new cells and/or formation of new blood vessels is a therapeutically-desirable goal for the prophylaxis or treatment of numerous conditions and diseases, including such major pathologies as myocardial and other forms of ischemia, and wound healing, as well as adjunctive therapy to increase the success rate of, for example, organ transplants and skin grafts. The examples provided herein below are merely illustrative of the range of utilities of pharmaceutical compositions comprising proliferation promoting agents, which include but are not limited to angiogenic agents; such uses are known to the skilled artisan; moreover, various citations referred to herein, and incorporated by reference, offer guides to certain of the uses mentioned here.

Poorly perfused tissues and organs, such as the heart as a sequela of myocardial infarction, other ischemic organs for example as a result of diabetic macro- and microvasculopathy, as well as to promote wound healing, organ transplantation, acceleration of endothelial cell growth and vascularization of vascular grafts in order to promote integration of the graft, prevent graft failure due to reocclusion, and to enhance skin grafting, all of the foregoing are exemplary of desirable targets for increasing vascularization and uses of the angiogenic agents herein. Enhanced vascularization of a chronically ischemic organ is a therapeutically beneficial goal.

The term "angiogenesis," as used herein, refers to the formation of blood vessels. Specifically, angiogenesis is a multistep process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175–203 (1985)). These processes are controlled by soluble factors and by the extracellular matrix (see Ingber et al., Cell, Vol. 58, pp. 803–805 (1985)). The agents of the invention may be administered in appropriate pharmaceutical compositions to the desired site in the body or target tissue or organ by any means that achieves the desired therapeutic effect. By way of non-limiting example, proliferation promoting agents including angiogenic agents may be administered locally, such as by injection or deposition of a pharmaceutical composition comprising the agent in a target tissue or organ, or by the implantation of a controlled release delivery device or matrix containing the agent in a suitable pharmaceutical composition, to achieve local effects. Such sites may be accessed surgically, or via transcutaneous catheterization to gain access to a tissue or organ through the major vasculature. For example, enhancing the perfusion of the ischemic heart may be achieved by use of a transcutaneous catheter that may be positioned to release the angiogenic agent of the invention into the coronary vasculature. Controlled and sustained release pharmaceutical compositions and devices comprising the aforementioned agents are fully embraced herein. Surgical or transcutaneous methods may also be used. These and other means for contacting the agents of the invention with the desired target cells, tissue or organs will be readily apparent to the skilled artisan.

The present invention is directed to pharmaceutical compositions of the above agents described in Formula I. The formulation of the instant compounds in appropriate vehicles or carriers or drug delivery systems is readily determinable by the skilled artisan, and all such methods of delivery are embraced herein. Examples are provided herein by way of illustration only, and are not intended to be limiting whatsoever.

The pharmaceutical compositions of the invention may be for admninistration for injection, or for oral, pulmonary, nasal or other forms of administration. In general, comprehended by the invention are pharmaceutical compositions comprising effective amounts of a low molecular weight component or components, or derivative products, of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in-vivo release, and rate of in vivo clearance of the present proteins and derivatives. See, e.g., Remington's Pharmaceutical Sciences, 18th Ed. (1990, Mack Publishing Co., Easton, Pa. 18042) pages 1435–1712 which is herein incorporated by reference. The compositions may be prepared in liquid form, or may be in dried powder, such as lyophilized form.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the component or components (or chemically modified forms thereof) and inert ingredients which allow for protection against the stomach environment if necessary for stability, and release of the active agent in the intestine.

Also specifically contemplated are oral dosage forms of the above-derivatized component or components. The component Of components may be chemically modified so that oral delivery of the derivative is efficacious. Generally, the chemical modification contemplated is the attachment of at least one moiety to the component molecule itself, where the moiety permits uptake into the blood stream from the stomach or intestine. Also desired is the increase in overall stability of the.component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367–383; Newmark, et al., 1982, J. Appl. Biochem. 4:185–189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment for acid-sensitive agents.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, lactose, anhydrous lactose, cellulose, sucrose, modified dextrans and starch. Certain inorganic salts may be also be used as fillers including calcium triphosphate, magnesium carbonate and sodium chloride, Some commercially available diluents are Fast-Flo, Emdex, STA-Rx 1500, Emcompress and Avicel.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the agent either alone or as a mixture in different ratios.

Additives which potentially enhance uptake of the agent are for instance the fatty acids oleic acid, linoleic acid and linolenic acid.

Controlled release oral formulation may be desirable. The agent could be incorporated into an inert matrix which permits release by either diffusion or leaching mechanisms, e.g., gums. Slowly degenerating matrices may also be incorporated into the formulation. Some enteric coatings also have a delayed release effect.

Other coatings may be used for the formulation. These include a variety of sugars which could be applied in a coating pan. The therapeutic agent could also be given in a film coated tablet and the materials used in this instance are dividedinto 2 groups. The first are the nonenteric materials and include methyl cellulose, ethyl cellulose, hydroxyethyl cellulose, methylhydroxyethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan-coater or in a fluidized bed or by compression coating.

Also contemplated- herein is pulmonary delivery of the present agent. The agent is delivered to the lungs of a mammal while inhaling and traverses across the lung epithelial lining to the blood stream. Other reports of this include Adjei et al., 1990, Pharmaceutical Research, 7:565–569; Adjei et al., 1990, International Journal of Pharmaceutics, 63:135–144 (leuprolide acetate); Braquet et al., 1989, Journal of Cardiovascular Pharmacology, 13(suppl. 5):143–146 (endothelin-1); Hubbard et al., 1989, Annals of Internal Medicine, Vol. III, pp. 206–212 (a1-antitrypsin); Smith et al., 1989, J. Clin. Invest. 84:1145–1146 (a-1-proteinase); Oswein et al., 1990, "Aerosolization of Proteins", Proceedings of Symposium on Respiratory Drug Delivery II, Keystone, Colorado, March, (recombinant human growth hormone); Debs et al., 1988, J. Immunol. 140:3482–3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Intravenous or other injectable forms of the compounds of the invention are also embraced herein, wherein the dosage form includes the agent in a suitable solution or reconstitutable form for injection.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the agent. Typically, each formulation is specific to the type of device employed and may involve the use of an appropriate propellant material, in addition to the usual diluents, adjuvants andior carriers useful in therapy. Also, the use of liposomes, microcapsules or microspheres, inclusion complexes, or other types of carriers is contemplated.

Formulations suitable for use with a nebulizer, either jet or ultrasonic, will typically comprise protein (or derivative) dissolved in water at a concentration of about 0.1 to 25 mg of agent per mL of solution. The formulation may also include a buffer and a simple sugar (e.g., for protein stabilization and regulation of osmotic pressure). The nebulizer formulation may also contain a surfactant.

Formulations for use with a metered-dose inhaler device will generally comprise a finely divided powder containing the agent suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the agent and may also include a bulking agent, such as lactose, sorbitol, sucrose, or mannitol in amounts which facilitate dispersal of the powder from the device, e.g., 50 to 90% by weight of the formulation. The agent should most advantageously be prepared in particulate form with an average particle size of less than 10 mm (or microns), most preferably 0.5 to 5 mm, for most effective delivery to the distal lung.

Nasal delivery of the agent is also contemplated. Nasal delivery allows the passage of the agent to the blood stream directly after administering the therapeutic product to the nose, without the necessity for deposition of the product in the lung. Formulations for nasal delivery include those with dextran or cyclodextran.

For controlled delivery, incorporation of the material into particulate preparations of polymeric compounds such as polylactic acid, polyglycolic acid, etc. or into liposomes may be used, or the use of a controlled release device, such as an implantable osmotic or other type of pump. Another form of a controlled release of this therapeutic is by a method based on the Oros therapeutic system (Alza Corp.), i.e. the drug is enclosed in a semipermeable membrane which allows water to enter and push drug out through a single small opening due to osmotic effects. Likewise, the skilled artisan will be amply aware of suitable delivery methods that may be extended to the agents of the invention to achieve the intended therapeutic goals of the invention.

The compounds of the invention may be delivered by intravenous, intraarterial, intraperitoneal, intramuscular, or subcutaneous routes of administration. A pharmaceutical composition for parenteral administration may be prepared using one or more of the compounds of Formula I, with a suitable diluent, excipient, or other components, to provide a stable and effective formulation for injection.

A subject in whom administration of a pharmaceutical composition of the invention in an effective therapeutic regiment for a disease or condition exemplified above, but not so limiting, is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

For all of the above molecules, as further studies are conducted, information will emerge regarding appropriate dosage levels for treatment of various conditions in various patients, and the ordinary skilled worker, considering the therapeutic context, age and general health of the recipient, will be able to ascertain proper dosing. The appropriate effective dosage of an agent of the invention may be readily determinable by following standard methods. Several animal models are described herein which model conditions and diseases encountered in the clinical setting, and as part of a drug development process, efficacious doses in animal studies, in particular, dose-response studies, are translated into appropriate doses for testing in humans, by following guidelines well known to those skilled in the art. Thus, an effective dose in a human may be determined following such industry-standard guidelines. As shown in the Examples, infra, a dosage approximately equal to the equivalent of 0.1 mg/kg/day to about 10 mg/kg/day, and more preferably, from about 0.5 mg/kg/day to about 5 mg/kg/day, is therapeutically effective in the disease model. Generally, for intravenous injection or infusion, or with a derivative of the component, dosage may be lower. The dosing schedule may vary, depending on the circulation half-life, and the formulation used.

As mentioned above, pharmaceutical compositions comprising the proliferation promoting agents including angiogenic agents of the invention may be used to promote endothelial cell and microvessel growth, with the goal of increasing vascularization and perfusion of tissues and organs in the body. They may also be used to promote growth of other cells types, such as those expressing c-met. Also as noted above, the agents may be locally applied or delivered to the desired site or sites. While the invention embraces any and all uses of angiogenic an generally proliferation promoting agents for humans and other mammals, some examples include treatment of ischemic tissues and organs, such as after injury, including myocardial damage after a heart attack, promoting vascularization of transplanted, reattached or translocated tissues or organs, such as following organ transplants, traumatic injury, promotion of wound healing, skin and other organ grafting, to name some examples. They are particularly useful for promoting the growth of endothelial cells in vascular grafts and transplants.

With regard to the compounds of Formula I herein, as used herein, the term "alkyl" means straight-chain, branched-chain or cyclo saturated aliphatic hydrocarbon groups preferably containing from one to about 6 carbon atoms. Representative of such straight-chain groups are methyl, ethyl, butyl, pentyl, hexyl and the like. Examples of branched-chain groups include isopropyl, isobutyl and t-butyl. Cycloalkyl includes groups such as but not limited to cyclopropyl, cyclobutyl, cyclopentyl and cyclohexyl. The term "aryl" refers to, for example, phenyl, biphenyl and naphthyl groups, which are optionally substituted by one or more halogen (F, Cl, Br and I), C1 to C4 alkyl, or C1 to C4 alkyloxy, where alkyloxy refers to an alkyl group as defined above attached to the remainder of the molecule by oxygen. Examples of alkyloxy include methoxy, ethoxy, propoxy, isopropoxy and the like. The term "heteroaryl" refers to heterocyclic groups containing 4–10 ring members and 1–3 heteroatoms selected from the group consisting of oxygen, nitrogen and sulfur. Examples include but are not limited to isoxazolyl, phenylisoxazolyl, furyl, pyrimidinyl, quinolyl, tetrahydroquinolyl, pyridyl, imidazolyl, pyrrolidinyl, 1,2,4-triazoylyl, thiazolyl, thienyl, and the like. The aryl or heteroaryl group may be optionally substituted by one or more halogen (F, Cl, Br and I), C1 to C4 alkyl, C1 to C4 alkyloxy as described above, trifluoromethyl, difluoromethyl, nitro, hydroxy, amine (optionally alkyl substituted), or another aryl or another heteroaryl group as described above.

The invention is directed to a pharmaceutical composition comprising a compound that modulates HGF/SF activity with the general formula I:

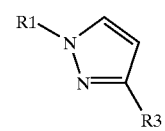

Formula I wherein

R1 is SO₂Alkyl, SO₂-Aryl, COAlkyl, COAryl, CONHAlkyl; or CONHAryl; and R3 is CHCH-heteroaryl; phenoxyphenyl; heteroaryl; or Aryl substituted heteroaryl; and a pharmaceutically-acceptable carrier, excipient or diluent.

Preferably, R1 may be SO₂Alkyl, wherein Alkyl is C1 to C4 straight-chained, branched or cyclo, most preferably SO₂CH₃; SO₂-Aryl, wherein Aryl is halo, C1–4 alkyl or alkyloxy substituted phenyl; COAlkyl, wherein alkyl is C1 to C6 straight-chained alkyl, branched alkyl or cycloalkyl, most preferably CO-t-Butyl; COAryl wherein Aryl is phenyl substituted with halo, C1–C4 alkyl or alkyloxy; CONHAlkyl wherein alkyl is C1 to C6 straight-chained alkyl, branched alkyl or cycloalkyl, most preferably CONHCH$_3$; or CONHAryl, wherein aryl is phenyl substituted with halo, C1 to C4 alkyl or C1 to C4 alkyloxy. R3 may be CHCH-heteroaryl, where in heteroaryl includes but is not limited to both cis and trans CHCH-3-thienyl, CHCH-2-furyl and CHCH-3-furyl, and substituted CHCH-thienyl and CHCH-furyl, most preferably CHCH-2-thienyl; phenoxyphenyl; heteroaryl; or aryl substituted heteroaryl.

The invention includes pharmaceutical compositions comprising a compound of Formula I. Certain of the compounds of Formula I are novel, and the present invention is also inclusive of pharmaceutical compositions comprising all such novel compounds. Moreover, the invention is also directed to a pharmaceutical composition comprising at least one compound of Formula I, in a pharmaceutically-acceptable carrier, for any of the uses described herein.

The invention is also directed to compounds of Formula I. These pyrazoles may be synthesized by several methods. In method A, illustrated below, 3-bromopyrazole (commercially available) will under go alkylation or acylation by reaction with an acyl chloride or alkyl halide in a suitable polar aprotic solvent such as dichloromethane and base such triethylamine to form intermediate 2. Coupling reaction with a boronic acid, using a palladium catalyst, base such as K2CO3 or CsCO3, and warming in an aprotic solvent such as benzene, toluene, or xylene will provide target pyrazoles 3. Alternatively, 3-bromopyrazole 2 may be coupled with vinyl compounds in the presence of a catalyst prepared in situ from 2.5% Pd(AcO)2 with 5% m.sulfonated triphenylphosphine (TPPTS) in an aqueous solvent such as water and ethanol. (Ref Genet, J. P., Blart, E.; Savignac, M., Synlett, 1992, 715–717).

For example, using Method A, below, for the preparation of (4-chlorophenyl)[3-(2-(2-thienyl)vinyl)-1H-pyrazol-1-yl]methanone (also referred to herein as C6), one may react 3-bromopyrazole with 4-chlorobenzoyl chloride (commercially available, for example, from Aldrich Chemical Co., Milwaukee, Wis.) to provide the first intermediate in Method A. Then reaction of this material with E-2-(thienylethenyl)boronic acid (commerically available, for example, from Combi-Blocks Inc., San Diego, Calif.) forms the desired product. Other compounds may be likewise prepared from the corresponding benzoyl chlorides as well an many different types of boronic acid analogs that are commercially available or readily synthesized.

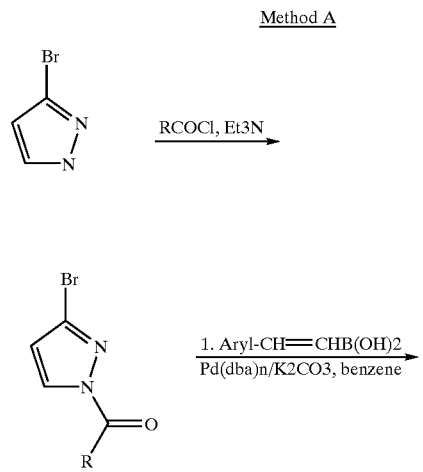

Method A

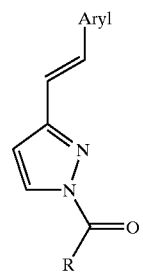

In Method B, depicted below, cinnamaldehydes undergo reaction with hydrazides to form hydrazone intermediates. The dianion of the corresponding hydrazones undergo reaction with esters, amides, acid anhydrides, acid chlorides and alkyl carbonates to forn target pyrazoles. (ref. Tetrahedron Lett. 1983, 24(31), 3239–3242.

Method B

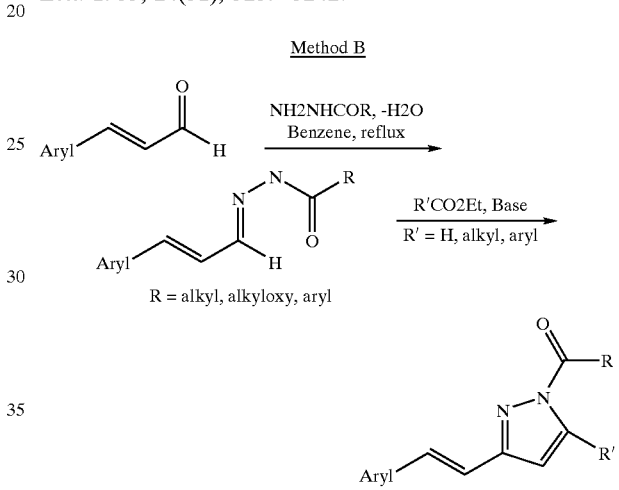

The foregoing are merely exemplary of synthetic routes to these compounds.

These compounds generally exhibit HGF/SF stimulatory or agonist activity. Non-limiting examples of compounds of Formula I, with formulae and molecular weights, include

| Chemical name | Formula | Molecular weight |
|---|---|---|
| (4-chlorophenyl)[3-(2-(2-thienyl)vinyl)-1H-pyrazol-1-yl]methanone (also referred to herein as C6) | $C_{16}H_{11}ClN_2OS$ | 314.80 |
| 1-(methylsulfonyl)-3-(2-(2-thienyl)vinyl)-1H-pyrazole | $C_{10}H_{10}N_2O_2S_2$ | 254.33 |
| 2,2-dimethyl-1-(3-(2-(2-thienyl)vinyl-1H-pyrazole-1-yl)propan-1-one | $C_{14}H_{16}N_2OS$ | 260.36 |
| N-methyl-3-(2-(2-thienyl)vinyl)-1H-pyrazole-1-carboxamide | $C_{11}H_{11}N_3OS$ | 233.29 |
| (4-chlorophenyl)(3-(3-phenylisoxazol-5-yl)-1H-pyrazol-1-yl)methanone | $C_{19}H_{12}ClN_3O_2$ | 349.78 |
| (4-chlorophenyl)(3-(3-(4-chlorophenyl)-5-methylisoxazol-4-yl)-1H-pyrazol-1-yl)methanone | $C_{20}H_{13}Cl_2N_3O_2$ | 398.25 |
| (4-chlorophenyl)(3-(5-(2-thienyl)-2-thienyl)-1H-pyrazol-1-yl)methanone | $C_{18}H_{11}ClN_2OS_2$ | 370.88 |
| (2,4-dichlorophenyl)(3-(5-(2,4-difluorophenyl)-2-furyl)-1H-pyrazol-1-yl)methanone | $C_{20}H_{10}Cl_2F_2N_2O_2$ | 419.22 |

-continued

| Chemical name | Formula | Molecular weight |
|---|---|---|
| N-phenyl-3-(2-(2-thienyl)vinyl)-1H-pyrazole-1-carboxamide | $C_{16}H_{13}N_3OS$ | 295.37 |
| (4-chlorophenyl)(3-(2-(5-(2-thienyl)-2-thienyl)-4-methyl-1,3-thiazol-5-yl)-1H-pyrazol-1-yl)methanone | $C_{22}H_{14}ClN_3OS_3$ | 468.02 |
| (3-benzhydryl-1H-pyrazol-1-yl)(4-chlorophenyl)methanone | $C_{23}H_{17}ClN_2O$ | 372.86 |
| N-(4-chlorophenyl)-3-(2-(2-thienyl)vinyl)-1H-pyrazole-1-carboxamide | $C_{16}H_{12}ClN_3OS$ | 329.81 |
| (4-chlorophenyl)(3-(2-methylimidazo(1,2-a)pyridin-3-yl)-1H-pyrazol-1-yl)methanone | $C_{18}H_{13}ClN_4O$ | 336.78 |
| 2-chloro-6-(4-(1-(4-chlorobenzyl)-1H-pyrazol-3-yl)phenoxy)benzonitrile | $C_{23}H_{13}Cl_2N_3O_2$ | 434.28 |
| 1-((4-chlorophenyl)sulfonyl)-3-(2-(2-thienyl)vinyl)-1H-pyrazole | $C_{15}H_{11}ClN_2O_2S_2$ | 350.85 |

The invention is also directed to novel compounds of Formula I, above.

The invention is also directed to methods for treating a mammalian animal for a disease or condition described above by administering to the animal an effective amount of a compound of Formula I, described hereinabove, to achieve the intended purpose.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Pharmaceutical Compositions

| Compound of Formula I | 50 mg |
|---|---|
| Magnesium stearate | 10 mg |
| Sorbitol | 200 mg |

A solution for intravenous administration may be prepared from:

| Compound of Formula I | 10 mg |
|---|---|
| Saline | 100 cc |

EXAMPLE 2

HGF/SF-like Cellular Proliferative Activity of a Compound of the Invention

Using the endothelial cell proliferation assay described above, the compound (4-chlorophenyl)[3-(2-(2-thienyl)vinyl)-1H-pyrazol-1-yl]methanone was shown to increase HUVEC proliferation by two to five fold. The specificity of the stimulation of endothelial cell growth by the compound as measured by $^3$H-thymidine incorporation was tested by pre-incubation of cells with the HGF/SF receptor c-met. In FIG. 1, the first bar represents control cells; the second bar (4-chlorophenyl)[3-(2-(2-thienyl)vinyl)-1H-pyrazol-1-yl] methanone at 6 microgram/ml; and the third bar: (4-chlorophenyl)[3-(2-(2-thienyl)vinyl)-1H-pyrazol-1-yl] methanone at 6 microgram/ml plus c-met receptor, 100 microgram/ml. (4-Chlorophenyl)[3-(2-(2-thienyl)vinyl)-1H-pyrazol-1-yl]methanone by itself stimulated $^3$H-thymidine incorporation by 84%. Thus, (4-chlorophenyl) [3-(2-(2-thienyl)vinyl)-1H-pyrazol-1-yl]methanone is as effective as HGF/SF in stimulating HUVEC proliferation. In the presence of c-met, the (4-chlorophenyl)[3-(2-(2-thienyl) vinyl)-1H-pyrazol-1-y]methanone stimulation of $^3$H-thymidine incorporation was inhibited by 75%. In another related experiment, (4-chlorophenyl)[3-(2-(2-thienyl)vinyl)-1H-pyrazol-1-yl]methanone (12 microgram/ml) was incubated with the initial target molecule C-met receptor (5 microgram/ml) for 30 min and then added to the cells. Compound-induced EC proliferation was blocked by 40% in the presence of C-met receptor.

EXAMPLE 3

Figure 2B:
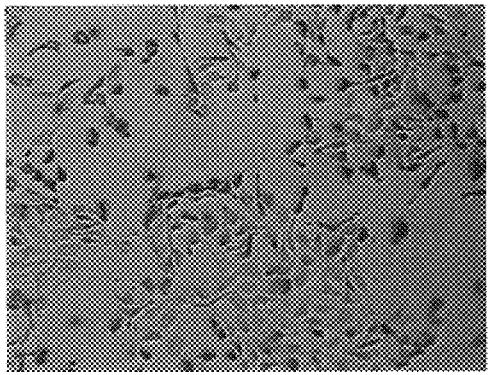

Scatter of MDCK Cells (4-Chlorophenyl)[3-(2-(2-thienyl)vinyl)-1H-pyrazol-1-yl]methanone was further tested for HGF/SF activity in a standard scatter assay that is specific for HGF/SF. The ability to scatter was demonstrated for the first time using a non-peptide candidate compound. Scatter of MDCK cells by (4-chlorophenyl)[3-(2-(2-thienyl)vinyl)-1H-pyrazol-1-yl] methanone further demonstrates that its actions are mediated through stimulation of the c-met receptor. As shown in FIG. 2, the compound caused scattering of MDCK cells similar to that seen with HGF/SF. FIG. 2A: Control cells; FIG. 2B: (4-chlorophenyl)[3-(2-(2thienyl)vinyl)-1H-pyrazol-1-yl] methanone, 6 microgram/ml.

EXAMPLE 4

Figure 3:
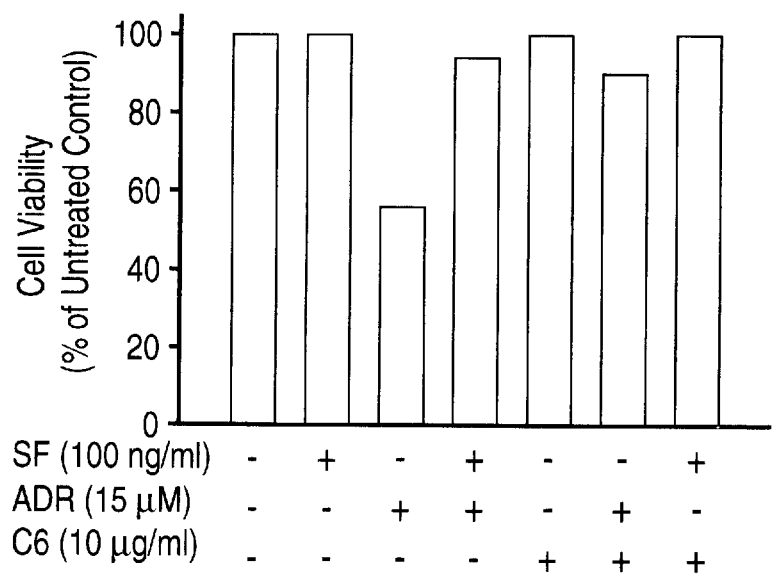
FIG. 3 shows the protection of MDCK cells from adriamycin-induced apoptosis by (4-chlorophenyl)[3-(2-(2-thienyl)vinyl)-1H-pyrazol-1-yl]methanone.

Anti-apoptotic Activity of (4-Chlorophenyl)[3-(2-(2-thienyl)vinyl)-1H-pyrazol-1-yl]methanone HGF/SF has significant anti-apoptotic activity in a number of cultured cell lines. Using the MTT cell viability assay the ability of (4-chlorophenyl)[3-(2-(2-thienyl)vinyl)-1H-pyrazol-1-yl]methanone to protect cells from adriamycin-induced apoptosis was evaluated. Like HGF/SF, (4-chlorophenyl)[3-(2-)2-thienyl)vinyl)-1H-pyrazol-1-yl] methanone was able to significantly block adriamycin-induced apoptosis in MDCK cells (FIG. 3). Cell viability was unchanged by either HGF/SF alone (column 2), (4-chlorophenyl)[3-(2-(2-thienyl)vinyl)-1H-pyrazol-1-yl] methanone alone (column 5) or HGF/SF and (4-chlorophenyl)[3-(2-(2-thienyl)vinyl)-1H-pyrazol-1-yl] methanone combined (column 7). Adriamycin (15 mM) decreased cell viability to 56% of control (column 3). Treatment with either HGF/SF (column 4) or (4-chlorophenyl)[3-(2-(2-thienyl)vinyl)-1H-pyrazol-1-yl] methanone (column 6) effected nearly complete (94%) protection from adriamycin-induced apoptosis.

In another cell line, 90% protection was afforded by (4-chlorophenyl)[3-(2-(2-thienyl)vinyl)-1H-pyrazol-1-yl] methanone.

EXAMPLE 5

Figure 4:
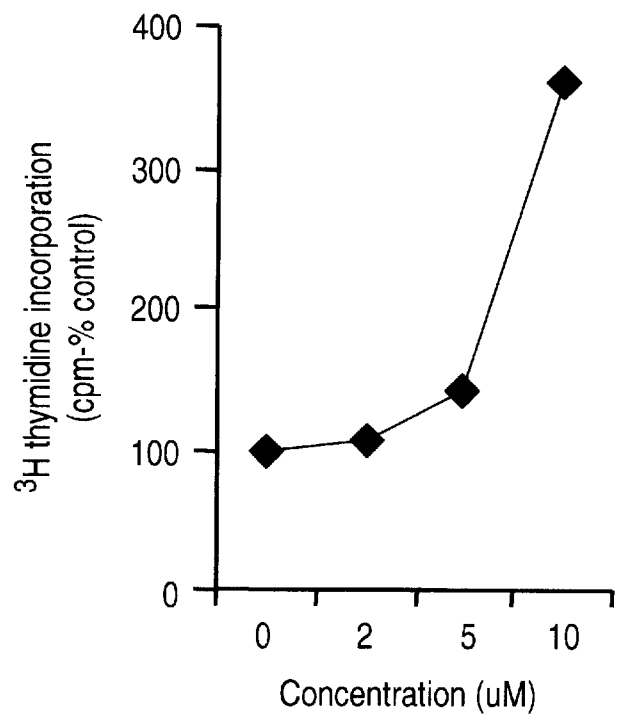
FIG. 4 shows a dose-response curve of the stimulation of endothelial cell proliferation by (4-chlorophenyl)[3-(2-(2-thienyl)vinyl)-1H-pyrazol-1-yl]methanone.

Effect of (4-Chlorophenyl)(3-(2-(2-thienyl)vinyl)-1H-pyrazol-1-yl-methanone on HUVEC Proliferation FIG. 4 shows a dose-response relationship between the level of level (4-chlorophenyl)(3-(2-(2-thienyl)vinyl)-1H-pyrazol-1-yl-methanone and HUVEC proliferation.

EXAMPLE 6

In Vivo Blood Flow Improvement Assay

Figure 5:
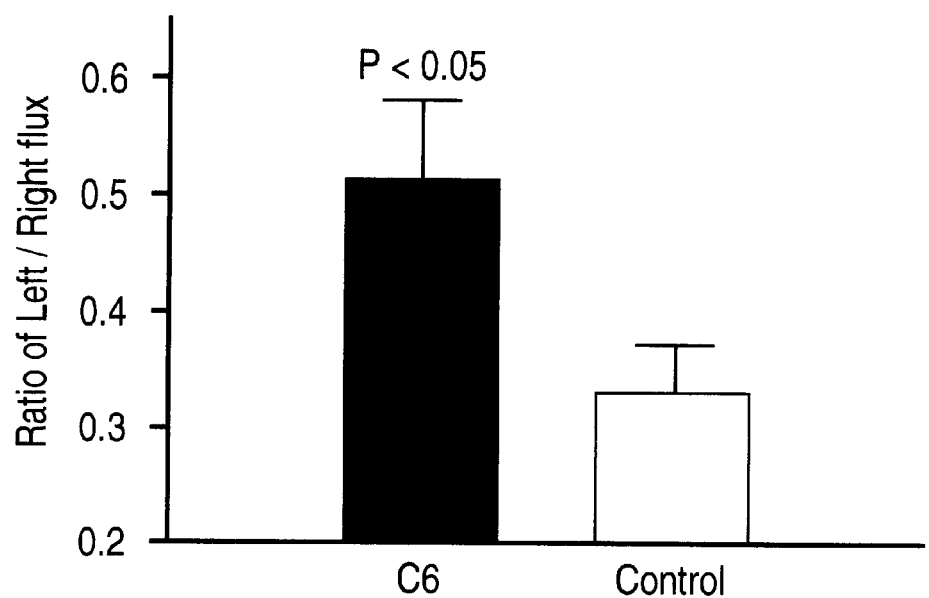
FIG. 5 shows improved blood flow in mice following removal of the femoral artery after administration of a.pharmaceutical compositions comprising (4-chlorophenyl)[3-(2-(2-thienyl)vinyl)-1H-pyrazol-1-yl]methanone.

FIG. 5 shows the results of an in-vivo experiment in which a pharmaceutical composition comprising (4-chlorophenyl)[3-(2-(2-thienyl)vinyl )-1H-pyrazol-1-yl]methanone was administered to mice for seven days following removal of the femoral artery. The results show significant improvement in blood flow with the compound.

EXAMPLE 7

Other Compounds With Activities

In a similar manner as described above, the following compounds related were evaluated for stimulation of endothelial cell proliferation. Three different rounds of testing were performed.

| Compound | Stimulation/Inhibition at 5 micrograms/ml | Stimulation/Inhibition at 10 micrograms/ml |
| --- | --- | --- |
| 1-(methylsulfonyl)-3-(2-(2-thienyl)vinyl)-1H-pyrazole | 74% stimulation | Not significant |
| 2,2-dimethyl-1-(3-(2-(2-thienyl)vinyl)-1H-pyrazole-1-yl)propan-1-one | No effect | 55% stimulation |
| N-methyl-3-(2-(2-thienyl)vinyl)-1H-pyrazole-1-carboxamide | 70% stimulation | 42% stimulation |
| (4-chlorophenyl)(3-(3-phenylisoxazol-5-yl)-1H-pyrazol-1-yl)methanone | 54% stimulation | 60% stimulation |
| (4-chlorophenyl)(3-(5-(2-thienyl)-2-thienyl)-1H-pyrazol-1-yl)methanone | 40% stimulation | 40% stimulation |
| N1-phenyl-3-(2-(2-thienyl)vinyl)-1H-pyrazole-1-carboxamide | 40% stimulation | Not significant |
| (4-chlorophenyl)(3-(2-(5-(2-thienyl)-2-thienyl)-4-methyl-1,3-thiazol-5-yl)-1H-pyrazol-1-yl)methanone | 20% stimulation | 33% stimulation |
| (3-benzhydryl-1H-pyrazol-1-yl)(4-chlorophenyl)methanone | No effect | 25% stimulation |
| N1-(4-chlorophenyl)-3-(2-(2-thienyl)vinyl)-1H-pyrazole-1-carboxamide | No effect | 55% stimulation |
| 2-chloro-6-(4-(1-(4-chlorobenzyl)-1H-pyrazol-5-yl)phenoxy)benzonitrile | 60% stimulation | 90% stimulation |

EXAMPLE 8

Figure 6:
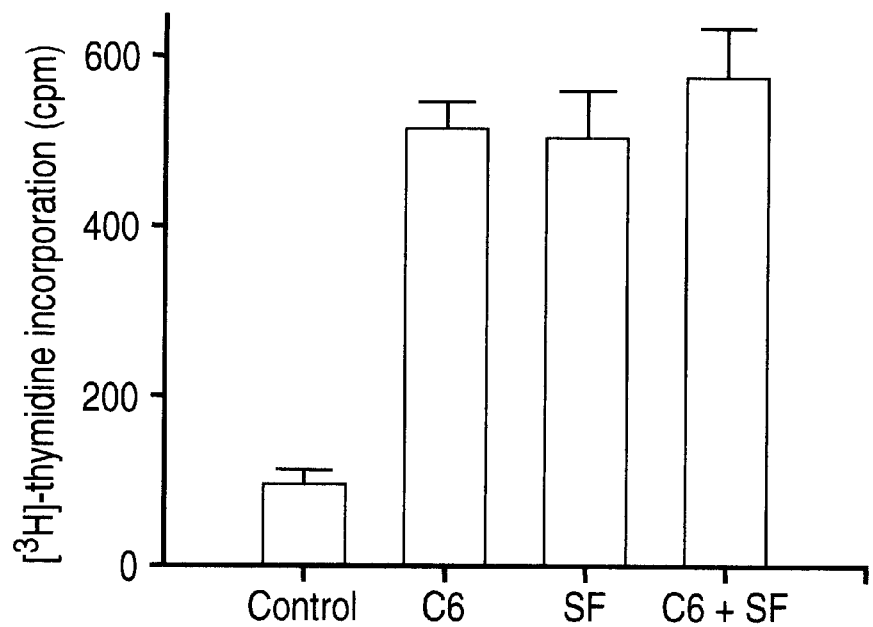
FIG. 6 shows the stimulation of 3H-thymidine incorporation into HUVEC by (4-chlorophenyl)[3-(2-(2-thienyl)vinyl)-1H-pyrazol-1-yl]methanone.

Stimulation of Endothelial Cell Proliferation by (4-Chlorophenyl)[3-(2-(2-thienyl)vinyl)-1H-pyrazol-1-yl]methanone One of the compounds identified with HGF/SF-like activity, (4-chlorophenyl)[3-(2-(2-thienyl)vinyl)-1H-pyrazol-1-yl]methanone, was able to stimulate endothelial cell proliferation in vitro (FIG. 6: first bar: control cells; second bar (4-chlorophenyl)[3-(2-(2-thienyl)vinyl)-1H-pyrazol-1-yl]methanone, 38 mM; third bar: HGF/SF, 20 ng/ml; fourth bar: (4-chlorophenyl)[3-(2-(2-thienyl)vinyl)-1H-pyrazol-1-yl]methanone+HGF/SF). The specificity of the stimulation by this compound of growth of HUVECs by $^3$H-thymidine incorporation was tested by pre-incubation of cells with the HGF/SF receptor c-met. (4-Chlorophenyl)[3-(2-(2-thienyl)vinyl)-1H-pyrazol-1-yl]methanone by itself stimulated $^3$H-thymidine incorporation by more than 5 fold (FIG. 6, bar 2). (4-chlorophenyl)[3-(2-(2-thienyl)vinyl)-1H-pyrazol-1-yl]methanone is as effective as HGF/SF in stimulating HUVEC proliferation. In the presence of c-met the (4-chlorophenyl)[3-(2-(2-thienyl)vinyl)-1H-pyrazol-1-yl]methanone stimulation of $^3$H-thymidine incorporation was inhibited by 75%. Scattering of MDCK cells in culture is a known specific effect of scatter factor and (4-chlorophenyl)[3-(2-(2-thienyl)vinyl)-1H-pyrazol-1-yl]methanone also has this ability, the first demonstration of this activity in a non-peptide compound. (4-Chlorophenyl)[3-(2-(2-thienyl)vinyl)-1H-pyrazol-1-yl]methanone, like HGF/SF, did not stimulate the growth of fibroblast cell lines and both showed similar inhibitory effects in HepG2 hepatoma cell lines.

EXAMPLE 9

Figure 7:
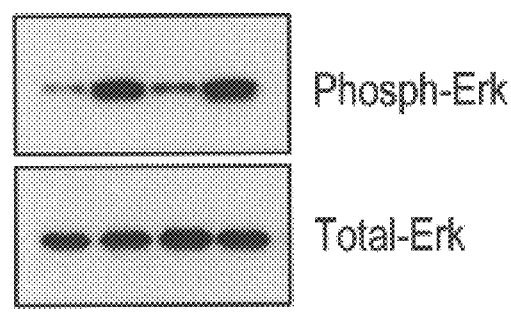
FIG. 7 depicts the phosphorylation of Erk by HGF/SF and (4-chlorophenyl)[3-(2-(2-thienyl)vinyl)-1H-pyrazol-1-yl]methanone.

(4-Chlorophenyl)[3-(2-(2-thienyl)viny)-1H-pyrazol-1-yl]Methanone Causes Phosphorylation of c-met and Erk Using immunoprecipitation and Western blotting we were able show that like HGF/SF, (4-chlorophenyl)[3-(2-(2-thienyl)vinyl)-1H-pyrazol-1-yl]methanone causes phosphorylation of the signaling protein Erk (FIG. 7). Both HGF/SF (lane 4) and (4-chlorophenyl)[3-(2-(2-thienyl)vinyl)-1H-pyrazol-1-yl]methanone (lane 2) showed significant amounts of phosphorylated Erk compared to unstimulated control cells (lane 1). A small molecule antagonist, (4-(2-chloro-6-fluorobenzyl)-3,5-dimethyl-1H-pyrazole-1-yl)(3-(2,6-dichlorophenyl)-5-methylisoxazol-4-yl)methanone had no effect on phosphorylation of Erk (Lane 3). Total Erk is shown on the bottom.

EXAMPLE 10

Wound Healing Studies

Figure 8:
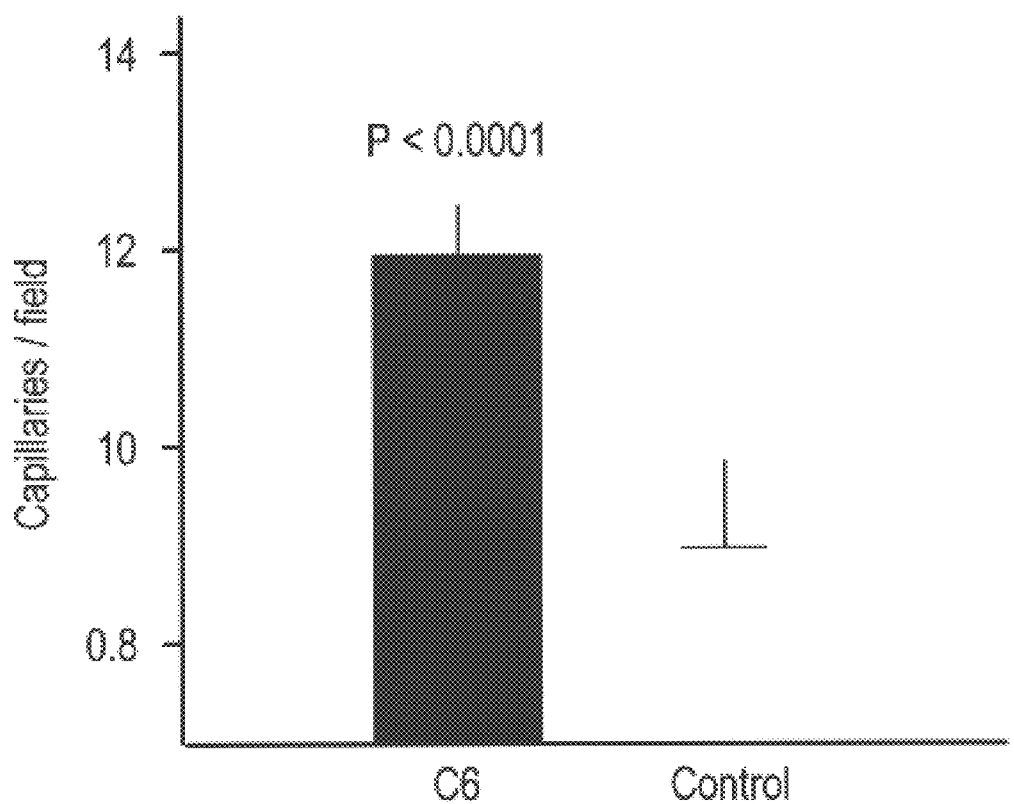
FIG. 8 demonstrates the efficacy of a pharmaceutical composition comprising (4-chlorophenyl)[3-(2-(2-thienyl)vinyl)-1H-pyrazol-1-yl]methanone in a pig wound healing model.

The angiogenic properties of a pharmaceutical composition comprising (4-chlorophenyl)[3-(2-(2-thienyl)vinyl)-1H-pyrazol-1-yl]methanone were further tested in a pig model of wound healing. Full thickness 8-mm skin wounds were produced in pigs and five days later the wounds were excised, stained with H&E and blood vessels counted in five areas from each section under high power. Wounds treated with (4-chlorophenyl)[3-(2-(2-thienyl)vinyl)-1H-pyrazol-1-yl]methanone (500 micrograms) demonstrated a 33% greater density of blood vessels compared to vehicle-treated (DMS) controls (FIG. 8).

EXAMPLE 11

Increase in Capillary Numbers by (4-Chlorophenyl)[3-(2-(2-thienyl)vinyl)-1H-pyrazol-1-yl]methanone.

Mice were subjected to unilateral hindlimb ischemia and treated with either the HGF/SF agonist, (4-chlorophenyl)[3-(2-(2-thienyl )vinyl)-1H-pyrazol-1-yl]methanone (25 micrograms/day) or vehicle for either two or three weeks prior to sacrifice. Hindlimb muscles were frozen in liquid nitrogen and capillaries stained by the alkaline phosphatase technique and the number of capillaries per muscle fiber counted in 6 to 12 random areas of the muscle by a blinded observer.

Figure 9:
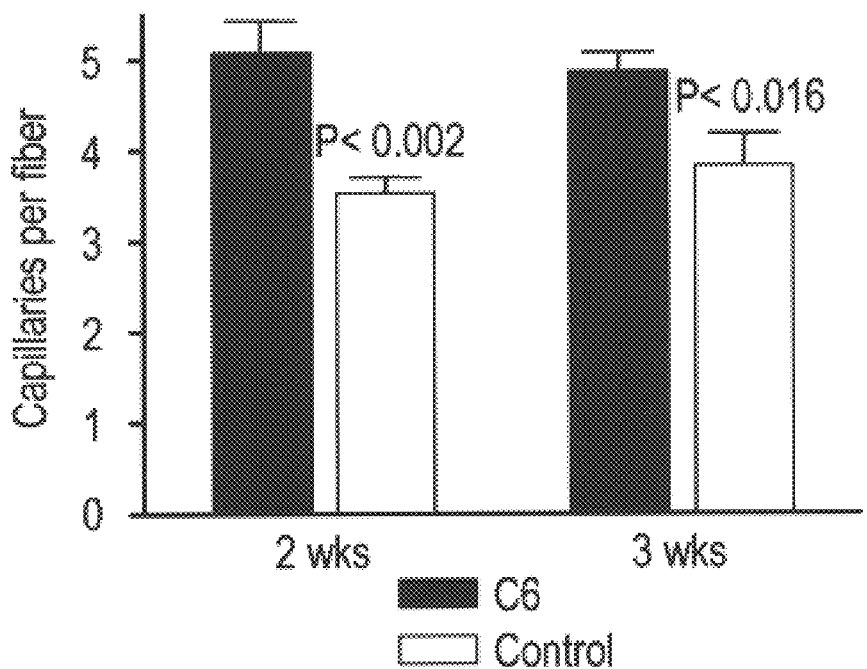
FIG. 9 shows the ability of a pharmaceutical composition comprising (4-chlorophenyl)[3-(2-(2-thienyl)vinyl)-1H-pyrazol-1-yl]methanone to increase capillary number in the ischemic mouse hindlimb.

Recovery in mice with hindlimb ischemia by increasing the number of capillaries in the ischemic muscle was observer (FIG. 9). At 2 weeks there was a 42% greater number of capillaries per muscle fiber in (4-chlorophenyl)[3-(2-(2-thienyl)vinyl)-1H-pyrazol-1-yl]methanone-treated mice compared to vehicle treated controls. This increased number of capillaries persisted at 3 weeks, the last time point for which samples were analyzed.

EXAMPLE 12

Figure 10:
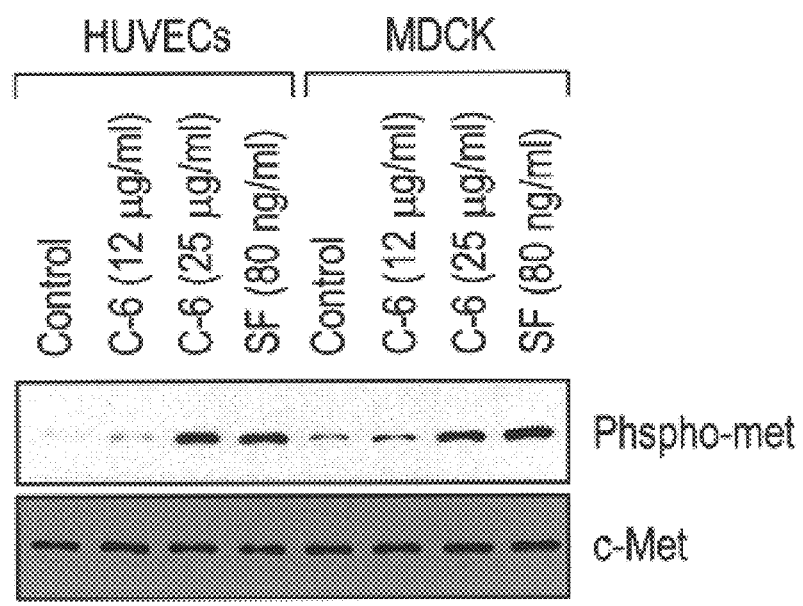
FIG. 10 depicts the dose-dependent phosphorylation of HUVECs and MDCK cells by (4-chlorophenyl)[3-(2-(2-thienyl)vinyl)-1H-pyrazol-1-yl]methanone.

(4-Chlorophenyl)[3-(2-(2-thienyl)vinyl)-1H-pyrazol-1-yl]methanone Produces a Dose-dependent Phosphorylation of C-met Studies of c-met phosphorylation have been extended to demonstrate that the phosphorylation is dose-related and occurs in both HUVECs as well as MDCK cells (FIG. 10). HUVECs (left set) or MDCK cells (right set) were treated with either HGF/SF or (4-chlorophenyl)[3-(2-(2-thienyl)vinyl)-1H-pyrazol-1-yl]methanone, solubilized lysates were prepared from cells and immunoprecipitation of phosphorylated c-met and total c-met using specific antibodies was performed using standard techniques. Immunoprecipitates were separated on SDS-polyacrylamide gels and proteins were transferred to nitrocellulose membranes and detection of phosphorylated (top) and total c-met (bottom) was performed using an ECL chemiluminescence system (Amersham). Both HGF/SF and (4-chlorophenyl)[3-(2-(2-thienyl)vinyl)-1H-pyrazol-1-yl]methanone showed significant amounts of phosphorylated c-met compared to unstimulated control cells. Total c-met is shown on the bottom.

This result further substantiates the findings that, like HGF/SF, (4-chlorophenyl)[3-(2-(2-thienyl)vinyl)-1H-pyrazol-1-yl]methanone produces its effects through activation of the c-met receptor.

EXAMPLE 13

(4-Chlorophenyl)[3-(2-(2-thienyl)vinyl)-1H-pyrazol-1-yl]methanone Reduces Hindlimb Ischemia in NOD Mice.

Figure 11:
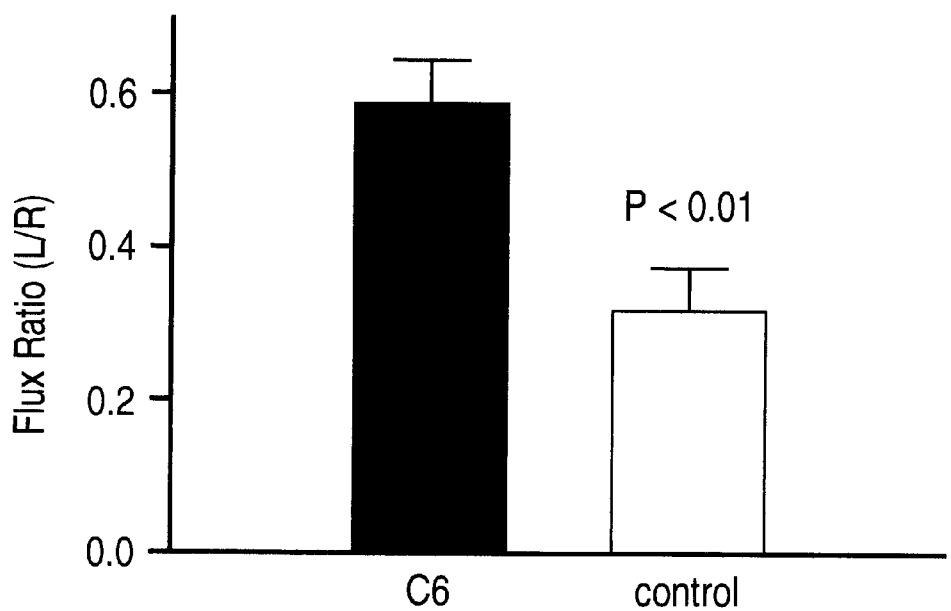
FIG. 11 shows a positive effect on hindlimb ischemia in diabetic mice by (4-chlorophenyl)[3-(2-(2-thienyl)vinyl)-1H-pyrazol-1-yl]methanone administration.

Female non-obese diabetic mice (NOD) were subjected to hindlimb ischemia by removal of the left femoral artery under ketamine/xylazine anesthesia. Mice were injected daily for four weeks with either (4-chlorophenyl)[3-(2-(2-thienyl)vinyl)-1H-pyrazol-1-yl]methanone (25 micrograms) or vehicle (RPMI 1640+1% BSA). Hindlimb blood flow was measured using a Laser Doppler imager 7 days later. In FIG. 11, the y-axis represents the ratio of flux in the left, ischemic limb to flux in the right, non-ischemic limb. At 7 days mice injected with (4-chlorophenyl)[3-(2-(2-thienyl)vinyl)-1H-pyrazol-1-yl]methanone (n=7) showed recovery to 59±6% of the non-ischemic side compared to 32±6% for control animals injected with vehicle (n=8) ($P<0.01$).

EXAMPLE 14

Figure 12:
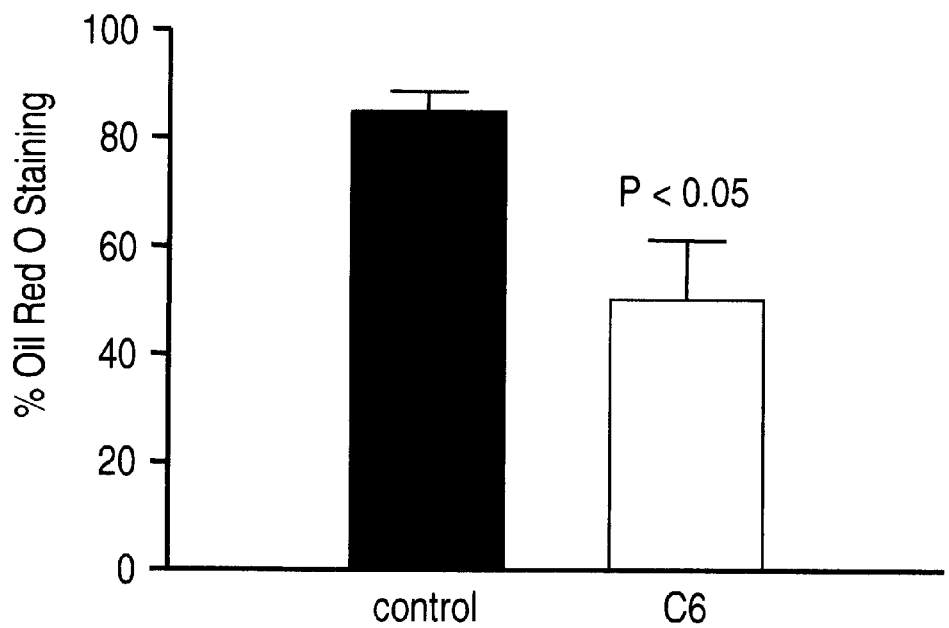
FIG. 12 demonstrates the reduction in lipid accumulation in the aortas of Apo E-null mice as a result of treatment with (4-chlorophenyl)[3-(2-(2-thienyl)vinyl)-1H-pyrazol-1-yl]methanone.

(4-Chlorophenyl)[3-(2-(2-thienyl)vinyl)-1H-pyrazol-1-yl]methanone Decreases Neutral Lipid Accumulation in ApoE-null Mice Eight-week old Female ApoE-null mice were injected daily for four weeks with either (4-chlorophenyl)[3-(2-(2-thienyl)vinyl)-1H-pyrazol-1-yl]methanone (25 micrograms) or vehicle (RPMI 1640+1% BSA). The abdominal aortas were then removed and fixed in 10% formalin prior to staining with Oil Red O to visualize neutral lipids. Stained aortas were mounted on slides and scanned with a Hewlett Packard ScanJet 4c scanner. Dark red stained neutral lipids were measured using a computerized image analysis system (Universal Imaging Corp). Results are presented in FIG. 12 as the percentage of the aorta stained dark red. (4-Chlorophenyl)[3-(2-(2-thienyl)vinyl)-1H-pyrazol-1-yl]methanone treatment resulted in a significant decrease in lipid accumulation to 30±11% compared to 85±3% in vehicle treated mice ($P<0.05$).

EXAMPLE 15

Figure 13:
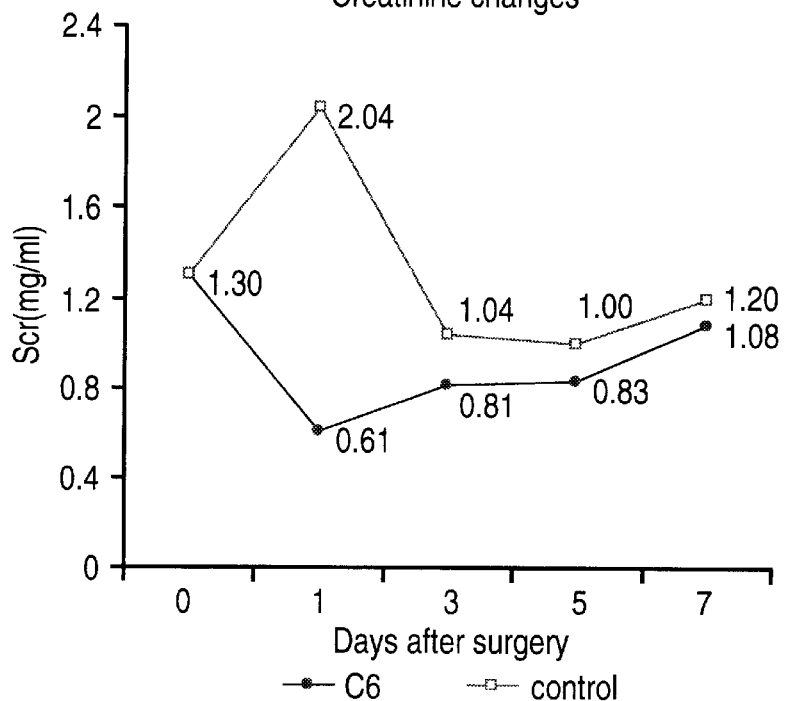
FIG. 13 shows that (4-chlorophenyl)[3-(2-(2-thienyl)vinyl)-1H-pyrazol-1-yl]methanone (also referred to herein as C6) prevents renal damage in a murine model of renal ischemia.

(4-Chlorophenyl)[3-(2-(2-thienyl)vinyl)-1H-pyrazol-1-yl]methanone Prevents Increased Creatinine by Renal Ischemia Male C57BL/6 mice were anesthetized with ketamine/xylazine and the left renal vessels were occluded with a clamp for 30 minutes. Following release of the occlusion, the right kidney was removed and the mouse was sutured closed. Mice were injected daily with either (4-chlorophenyl)[3-(2-(2-thienyl)vinyl)-1H-pyrazol-1-yl]methanone (25 micrograms) or vehicle (RPMI 1640+1% BSA) and blood samples collected over a period of 1 week for creatinine measurements to assess the renal damage in response to ischemia. As shown in FIG. 13, (4-chlorophenyl)[3-(2-(2-thienyl)vinyl)-1H-pyrazol-1-yl]methanone treatment prevented the initial large increase in creatinine that was observed in vehicle treated mice at day 1.

EXAMPLE 16

(4-Chlorophenyl)[3-(2-(2-thienyl)vinyl)-1H-pyrazol-1-yl]methanone Protects Against Mercury-induced Renal Damage Mercuric chloride ($HgCl_2$) was administered intraperitoneally (i.p.) to mice at a dosage of 7 mg/Kg body weight. Immediately thereafter, (4-chlorophenyl)[3-(2-(2-thienyl)vinyl)-1H-pyrazol-1-yl]methanone (25 micrograms/mouse) and control (DMSO) solution were given i.p. and continued daily for 3 days. Blood samples were harvested before the experiment and on the 2nd and 4th day after the $HgCl_2$ injection. Mice were sacrificed on the 4th day. Kidneys were collected for histology and molecular biology.

Figure 14:
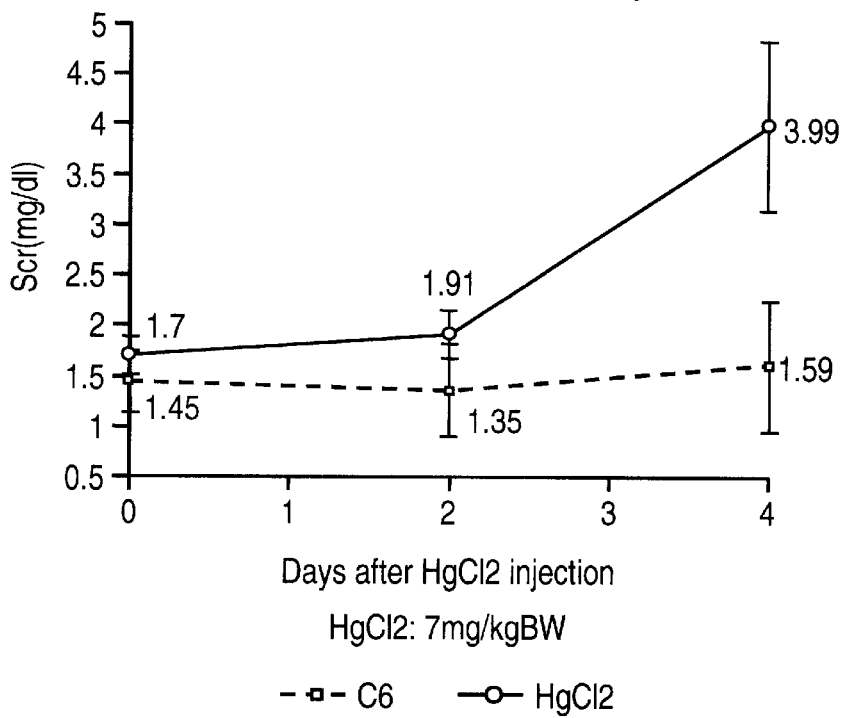
FIG. 14 shows the results of a study in which (4-chlorophenyl)[3-(2-(2-thienyl)vinyl)-1H-pyrazol-1-yl]methanone protected mice from mercuric chloride-induced renal damage.

FIG. 14 shows protection of kidneys from functional impairment by mercuric chloride. Untreated animals' renal function declined as shown by an increasing serum creatinine level. In contrast, treatment of animals with (4-chlorophenyl)[3-(2-(2-thienyl)vinyl)-1H-pyrazol-1-yl] methanone prevented the impairment.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

Bardelli, A., Ponzetto, C., Comoglio, P. M. (1994) Identification of functional domains in the hepatocyte growth factor and its receptor by molecular engineering. J. Biotechnol. 37:109–22.

Boros, P. and Miller, C. M. (1995) Hepatocyte growth factor: a multifunctional cytokine. Lancet 345, 293–5.

Gherardi, E., Hartmann, G., Hepple, J., Chirgadze, D., Srinivasan, N., Blundell, T. (1997) Domain structure of hepatocyte growth factor/scatter factor (HGF/SF). Ciba Found Symp 212:84–93.

Grant, D. S, Kleinman, H. K., Goldberg, I. D., Bhargava, M. M., Nickoloff, B. J., Kinsella, J. L., Polverini, P., Rosen, E. M. (1993) Scatter factor induces blood vessel formation in vivo. Proc. Nat. Acad. Sci. U S A 90:1937–41.

Jeffers, M., Rong, S., Woude, G. F. (1996) Hepatocyte growth factor/scatter factor-Met signaling in tumorigenicity and invasion/metastasis. J. Mol. Med. 74:505–13.

Kibbey, M. C., Grant, D. S. Auerbach, R. and Kleinman, H. K. (1992) Role of the SIKVAV site of laminin in promotion of angiogenesis and tumor growth: an in vivo Matrigel model. J. Natl. Can. Inst. 84, 1633–38.

Koivunen E, Wang, B. and Ruoslahti, E. (1994) Isolation of a highly specific ligand for the alpha 5 beta 1 integrin from a phage display library. J Cell Biol. 124, 373–380.

Liu, S., Julian, J., Carson, D. D. (1998) A peptide sequence of heparin/heparan sulfate (HP/HS)-interacting protein supports selective, high affinity binding of HP/HS and cell attachment. J. Biol. Chem. 273, 9718–26.

Lokker, N. A., Mark, M. R., Luis, E. A., Bennett, G. L., Robbins, K. A., Baker, J.B., Godowski, P. J. (1992) Structure-function analysis of hepatocyte growth factor: identification of variants that lack mitogenic activity yet retain high affinity receptor binding. EMBO J. 11:2503–10.

Matsumoto, K, and Nakamura, T. (1997) Hepatocyte growth factor (HGF) as a tissue organizer for organogenesis and regeneration. Biochem. Biophys. Res. Commun. 239, 639–44.

Morishita, R, Nakamura, S, Nakamura, Y, Aoki, M, Moriguchi, A, Kida, I, Yo, Y, Matsumoto, K, Nakamura, T, Higaki, J, Ogihara, T (1997) Potential role of an endothelium-specific growth factor, hepatocyte growth factor, on endothelial damage in diabetes. Diabetes 46:138–42.

Morishita, R., Nakamura, S., Hayashi, S., Taniyama, Y., Moriguchi, A., Nagano, T., Taiji, M., Noguchi, H., Takeshita, S., Matsumoto, K., Nakamura, T., Higaki, J., Ogihara, T. (1999) Therapeutic angiogenesis induced by human recombinant hepatocyte growth factor in rabbit hind limb ischemia model as cytokine supplement therapy. Hypertension 33:1379–84.

Moriyama, T., Kataoka, H., Koono, M., Wakisaka, S. (1999) Expression of hepatocyte growth factor/scatter factor and its receptor c-met in brain tumors: evidence for a role in progression of astrocytic tumors Int. J. Mol. Med. 3:531–6.

Naldini, L., Tamagnone, L., Vigna, E., Sachs, M., Hartmann, G., Birchmeier, W., Daikuhara, Y., Tsubouchi, H., Blasi, F., Comoglio, P. M. (1992) Extracellular proteolytic cleavage by urokinase is required for activation of hepatocyte growth factor/scatter factor. EMBO J. 11:4825–33.

Nicosa, R. F. and Ottinetti, A. (1990) Growth of microvessels in serum-free matrix culture of rat aorta. Lab. Invest. 63: 115–122.

O'Neil, K. T. and Hoess, R. H. (1995) Phage Display: Protein engineering by directed evolution Curr. Opin. Struc. Biol. 5, 443–449.

Pasqualini R, Koivunen, E. and Ruoslahti, E. (1995) A peptide isolated from phage display libraries is a structural and functional mimic of an RGD-binding site on integrins. J Cell Biol. 130, 1189–1196.

S. Paka, Goldberg, I. J., Choi, S. Y. Obunike, J., Saxena, U. Goldberg, I. D. and Pillarisetti, S. (1999) Perlecan mediates the anti-proliferative effect of apolipoprotein E on smooth muscle cells J. Biol. Chem. 274, 36403.

Saggio, I. And Laufer, R. (1993) Biotin binders selected from a random peptide library expressed on phage. Biochem. J. 293, 613–616.

Sakata, H, Stahl, S. J, Taylor, W. G, Rosenberg, J. M, Sakaguchi, K, Wingfield, P. T, and Rubin, J. S. (1997) Heparin binding and oligomerization of hepatocyte growth factor/scatter factor isoforms. Heparan sulfate glycosaminoglycan requirement for Met binding and signaling J Biol Chem 272, 9457–9463.

van der Voort, R., Taher, T. E., Wielenga, V. J., Spaargaren, M., Prevo, R., Smit, L., David, G., Hartmann, G., Gherardi, E., Pals, S. T. (1999) Heparan sulfate-modified CD44 promotes hepatocyte growth factor/scatter factor-induced signal transduction through the receptor tyrosine kinase c-met. J. Biol. Chem. 274, 6499–506.

Widersten, M. and Mannervik, B. (1995) Glutathione S transferase with novel active sites isolated by phage display from a library of random mutants. J. Mol. Biol. 250, 115–122.

Wrighton, N. C., Farrell, F. X., Chang, R., Kashyap, A. K., Barbone, F. P., Mulcahy, L. S., Johnson, D. L., Barrett, R. W., Jolliffe, L. K. and Dower, W. J. (1996) Small peptides as potent mimetics of the protein hormone erythropoietin. Science 273, 458–461.

What is claimed is:

1. A pharmaceutical composition comprising an effective HGF/SF activity modulating amount of a compound with the general formula:

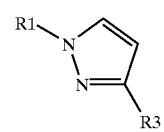

Formula I wherein

R1 is SO$_2$Alkyl, wherein alkyl is a C1 to C4 a straight chain, branched or a cycloalkyl group; SO$_2$-Aryl wherein aryl is halo, C1 to C4 alkyl or alkoxy substituted phenyl; COAlkyl, wherein alkyl is C1 to C6 straight chain alkyl, branched alkyl, or cycloalkyl; COAryl, wherein Aryl is phenyl substituted with halo, C1 to C4 alkyl or alkyloxy, trifluoromethyl, difluormethyl, nitro, hydroxy, amine, or another aryl or another heteroaryl; CONHAlkyl wherein alkyl is C1 to C6 straight chained alkyl, branched alkyl, or cycloalkyl; or CONHAryl, wherein aryl is a phenyl substituted with halo, C1 to C4 alkyl or C1 to C4 alkyloxy; and R3 is CHCH-heteroaryl; phenoxyphenyl; heteroaryl; or aryl substituted heteroaryl; and a pharmaceutically acceptable carrier, excipient, or diluent.

2. The pharmaceutical composition of claim 1 wherein R1 is SO$_2$CH$_3$, COAryl wherein Aryl is phenyl substituted with halo, or CONHCH$_3$ and R3 is CHCH-2-thienyl.

3. The pharmaceutical composition of claim 1 wherein said compound is (4-chlorophenyl)[3-(2-(2-thienyl)vinyl)-1H-pyrazol-1-yl]methanone;

1-(methylsulfonyl)-3-(2-(2-thienyl)vinyl)-1H-pyrazole;

2,2-dimethyl-1-(3-(2-(2-thienyl)vinyl)-1H-pyrazole-1-yl)propan-1-one;

N-methyl-3-(2-(2-thienyl)vinyl)-1H-pyrazole-1-carboxamide;

(4-chlorophenyl)(3-(3-phenylisoxazol-5-yl)-1H-pyrazol-1-yl)methanone;

(4-chlorophenyl)(3-(3-(4-chlorophenyl)-5-methylisoxazol-4-yl)-1H-pyrazol-1-yl)methanone;

(4-chlorophenyl)(3-(5-(2-thienyl)-2-thienyl)-1H-pyrazol-1-yl)methanone;

(2,4-dichlorophenyl)(3-(5-(2,4-difluorophenyl)-2-furyl)-1H-pyrazol-1-yl)methanone;

N1-phenyl-3-(2-(2-thienyl)vinyl)-1H-pyrazole-1-carboxamide;

(4-chlorophenyl)(3-(2-(5-(2-thienyl)-2-thienyl)-4-methyl-1,3-thiazol-5-yl)-1H-pyrazol-1-yl-methanone;

(3-benzhydryl-1H-pyrazol-1-yl)(4-chlorophenyl)methanone;

N1-(4-chlorophenyl)-3-(2-(2-thienyl)vinyl)-1H-pyrazole-1-carboxamide;

(4-chlorophenyl)(3-(2-methylimidazo(1,2-a)pyridin-3-yl)-1H-pyrazol-1-yl)methanone;

2-chloro-6-(4-(1-(4-chlorobenzyl)-1H-pyrazol-3-yl)phenoxy)benzonitrile; or 1-((4-chlorophenyl)sulfonyl)-3-(2-(2-thienyl)vinyl)-1H-pyrazole.

4. A compound with the general formula I:

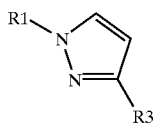

Formula I wherein:

R1 is $SO_2$Alkyl, wherein alkyl is a C1 to C4 straight chain, branched or a cycloalkyl group; $SO_2$-Aryl, wherein aryl is halo, C1 to C4 alkyl or alkoxy substituted phenyl; COAlkyl, wherein alkyl is C1 to C6 straight chain alkyl, branched alkyl, or cycloalkyl; COAryl, wherein Aryl is phenyl substituted with halo, C1 to C4 alkyl or alkyloxy, trifluoromethyl, difluormethyl, nitro, hydroxy, amine, or another aryl or another heteroaryl; CONHAlkyl wherein alkyl is C1 to C6 straight chained alkyl, branched alkyl, or cycloalkyl; or CONHAryl, wherein aryl is a phenyl substituted with halo, C1 to C4 alkyl or C1 to C4 alkyloxy; and R3 is CHCH-heteroaryl; phenoxyphenyl; heteroaryl; or aryl substituted heteroaryl.

5. The compound of claim 4 wherein R 1 is $SO_2CH_3$, COAryl wherein Aryl is phenyl substituted with halo, or CONHCH$_3$ and R3 is CHCH-2-thienyl.

6. The compound of claim 4 wherein said compound is (4-chlorophenyl)[3-(2-(2-thienyl)vinyl)-1H-pyrazol-1-yl]methanone;

1-(methylsulfonyl)-3-(2-(2-thienyl)vinyl)-1H-pyrazole;

2,2-dimethyl-1-(3-(2-(2-thienyl)vinyl)-1H-pyrazole-1-yl)propan-1-one;

N-methyl-3-(2-(2-thienyl)vinyl)-1H-pyrazole-1-carboxamide;

(4-chlorophenyl)(3-(3-phenylisoxazol-5-yl)-1H-pyrazol-1-yl)methanone;

(4-chlorophenyl)(3-(3-(4-chlorophenyl)-5-methylisoxazol-4-yl)-1H-pyrazol-1-yl)methanone;

(4-chlorophenyl)(3-(5-(2-thienyl)-2-thienyl)-1H-pyrazol-1-yl)methanone;

(2,4-dichlorophenyl)(3-(5-(2,4-difluorophenyl)-2-furyl)-1H-pyrazol-1-yl)methanone;

N1-phenyl-3-(2-(2-thienyl)vinyl)-1H-pyrazole-1-carboxamide;

(4-chlorophenyl)(3-(2-(5-(2-thienyl)-2-thienyl)-4-methyl-1,3-thiazol-5-yl)-1H-pyrazol-1-yl-methanone;

(3-benzhydryl-1H-pyrazol-1-yl)(4-chlorophenyl)methanone;

N1-(4-chlorophenyl)-3-(2-(2-thienyl)vinyl)-1H-pyrazole-1-carboxamide;

(4-chlorophenyl)(3-(2-methylimidazo(1,2-a)pyridin-3-yl)-1H-pyrazol-1-yl)methanone;

2-chloro-6-(4-(1-(4-chlorobenzyl)-1H-pyrazol-3-yl)phenoxy)benzonitrile; or 1-((4-chlorophenyl)sulfonyl)-3-(2-(2-thienyl)vinyl)-1H-pyrazole.

7. A method for prophylaxis or treatment of an ischemic condition in a mammal comprising administering to said mammal an effective amount of a pharmaceutical composition comprising a compound of Formula I:

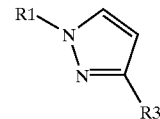

Formula I wherein:

R1 is $SO_2$Alkyl, wherein alkyl is a C1 to C4 straight chain, branched or a cycloalkyl group; $SO_2$-Aryl, wherein aryl is halo, C1 to C4 alkyl or alkoxy substituted phenyl; COAlkyl, wherein Alkyl is C1 to C6 straight chain alkyl, branched alkyl, or cycloalkyl; COAryl, wherein Aryl is phenyl substituted with halo, C1 to C4 alkyl or alkyloxy, trifluoromethyl, difluormethyl, nitro, hydroxy, amine, or another aryl or another heteroaryl; CONHAlkyl wherein alkyl is C1 to C6 straight chained alkyl, branched alkyl, or cycloalkyl; or CONHAryl, wherein aryl is a phenyl substituted with halo, C1 to C4 alkyl or C1 to C4 alkyloxy; and R3 is CHCH-heteroaryl; phenoxyphenyl; heteroaryl; or aryl substituted heteroaryl.

8. The method of claim 7 wherein R1 is $SO_2CH_3$, COAryl wherein Aryl is phenyl substituted with halo, or CONHCH$_3$ and R3 is CHCH-2-thienyl.

9. The method of claim 7 wherein said compound is (4-chlorophenyl)[3-(2-(2-thienyl)vinyl)-1H-pyrazol-1-yl]methanone;

1-(methylsulfonyl)-3-(2-(2-thienyl)vinyl)-1H-pyrazole;

2,2-dimethyl-1-(3-(2-(2-thienyl)vinyl)-1H-pyrazole-1-yl)propan-1-one;

N-methyl-3-(2-(2-thienyl)vinyl)-1H-pyrazole-1-carboxamide;

(4-chlorophenyl)(3-(3-phenylisoxazol-5-yl)-1H-pyrazol-1-yl)methanone;

(4-chlorophenyl)(3-(3-(4-chlorophenyl)-5-methylisoxazol-4-yl)-1H-pyrazol-1-yl)methanone;

(4-chlorophenyl)(3-(5-(2-thienyl)-2-thienyl)-1H-pyrazol-1-yl)methanone;

(2,4-dichlorophenyl)(3-(5-(2,4-difluorophenyl)-2-furyl)-1H-pyrazol-1-yl)methanone;

N1-phenyl-3-(2-(2-thienyl)vinyl)-1H-pyrazole-1-carboxamide;

(4-chlorophenyl)(3-(2-(5-(2-thienyl)-2-thienyl)-4-methyl-1,3-thiazol-5-yl)-1H-pyrazol-1-yl-methanone;

(3-benzhydryl-1H-pyrazol-1-yl)(4-chlorophenyl)
methanone;

N1-(4-chlorophenyl)-3-(2-(2-thienyl)vinyl)-1H-pyrazole-1-carboxamide;

(4-chlorophenyl)(3-(2-methylimidazo(1,2-a)pyridin-3-yl)-1H-pyrazol-1-yl)methanone;

2-chloro-6-(4-(1-(4-chlorobenzyl)-1H-pyrazol-3-yl)phenoxy)benzonitrile; or 1-((4-chlorophenyl)sulfonyl)-3-(2-(2-thienyl)vinyl)-1H-pyrazole.

10. The pharmaceutical composition of claim 1 wherein said CHCH-heteroaryl is cis or trans CHCH-3-thienyl, CHCH-2-furyl, CHCH-3-furyl, substituted CHCH-thienyl, or substituted CHCH-furyl.

11. The compound of claim 4 wherein said CHCH-heteroaryl is cis or trans CHCH-3-thienyl, CHCH-2-furyl, CHCH-3-furyl, substituted CHCH-thienyl, or substituted CHCH-furyl.

12. The method of claim 7 wherein said CHCH-heteroaryl is cis or trans CHCH-3-thienyl, CHCH-2-furyl, CHCH-3-furyl, substituted CHCH-thienyl, or substituted CHCH-furyl.

* * * * *